US012655396B2

(12) United States Patent
Dai et al.

(10) Patent No.: US 12,655,396 B2
(45) Date of Patent: Jun. 16, 2026

(54) CONSTRUCTION AND APPLICATION OF RECOMBINANT H5N8 SUBTYPE AVIAN INFLUENZA VIRUS CARRYING MAPPLE FLUORESCENCE REPORTER GENE

(71) Applicant: South China Agricultural University, Guangzhou (CN)

(72) Inventors: Manman Dai, Guangzhou (CN); Wei Song, Guangzhou (CN); Xiyue Chen, Guangzhou (CN); Ming Liao, Guangzhou (CN)

(73) Assignee: South China Agricultural University, Guangzhou (CN)

( * ) Notice: Subject to any disclaimer, the term of this patent is extended or adjusted under 35 U.S.C. 154(b) by 412 days.

(21) Appl. No.: 18/223,230

(22) Filed: Jul. 18, 2023

(65) Prior Publication Data

US 2024/0287466 A1 Aug. 29, 2024

(30) Foreign Application Priority Data

Feb. 28, 2023 (CN) .......................... 202310188363.1

(51) Int. Cl.
*C12N 7/00* (2006.01)
*A61K 35/76* (2015.01)
*C12N 15/86* (2006.01)

(52) U.S. Cl.
CPC ............... *C12N 7/00* (2013.01); *A61K 35/76* (2013.01); *C12N 15/86* (2013.01); *C12N 2760/16121* (2013.01); *C12N 2760/16122* (2013.01); *C12N 2760/16143* (2013.01)

(58) Field of Classification Search
CPC ........... C12N 7/00; C12N 15/86; A61K 35/76
See application file for complete search history.

(56) References Cited

FOREIGN PATENT DOCUMENTS

| | | |
|---|---|---|
| CN | 108517331 A | 9/2018 |
| CN | 109134662 A | 1/2019 |
| CN | 110184284 A | 8/2019 |
| CN | 110205321 A | 9/2019 |
| CN | 110218706 A | 9/2019 |
| CN | 113544267 A | 10/2021 |
| WO | 2012/059217 A1 | 5/2012 |

OTHER PUBLICATIONS

Perez, J. T., Garcia-Sastre, A., and Manicassamy, B., Insertion of a GFP Reporter Gene in Influenza Virus, 2013, Curr. Protoc. Microbiol., 15 (Year: 2013).*
Shaner et al., "Synthetic construct monomeric red fluorescent protein, complete cds", GenBank: DQ336160.2, pp. 1-2, May 5, 2008, URL: https://www.ncbi.nlm.nih.gov/nuccore/DQ336160.2/.
Yan et al., "Influenza A virus (A/chicken/China/JM01/2020(H5N8)) segment 8 nuclear export protein (NEP) gene, partial cds; and nonstructural protein 1 (NS1) gene, complete cds", GenBank: OP748416.1, pp. 1-2, Nov. 7, 2022, URL: https://www.ncbi.nlm. nih.gov/nuccore/OP748416.1/.
Liu Changting, Respiratory Medicine Clinical Q&A, People's Military Medical Press, pp. 228-229, ISBN 978-7-5091-3923-3; Jan. 2011, with an English translation.
First Office Action and Search Report issued by CNIPA for Chinese Patent Application No. 202310188363.1, mailed on Dec. 28, 2023, with an English translation.
Second Office Action issued by CNIPA for Chinese Patent Application No. 202310188363.1, mailed on May 31, 2024, with an English translation.

* cited by examiner

*Primary Examiner* — Benjamin P Blumel
*Assistant Examiner* — Kristina E. Ly
(74) *Attorney, Agent, or Firm* — Myers Wolin, LLC

(57) ABSTRACT

Disclosed is an NS protein, comprising an amino acid sequence from positions 1 to 217 of SEQ ID NO: 2, an amino acid sequence of an mApple fluorescence reporter gene and an amino acid sequence from positions 480 to 600 of SEQ ID NO: 2 linked in order. A recombinant H5N8 subtype avian influenza virus carrying an mApple fluorescence reporter gene is further disclosed, a genomic RNA of which is composed of 7 RNA fragments (PB2, PB1, PA, HA, NP, NA, M) identical to those of the genomic RNA of a wild H5N8 subtype avian influenza virus, and an RNA fragment 8 encoding the NS protein.
Compared with a wild H5N8 virus, the recombinant H5N8 subtype avian influenza virus has a weakened virulence, and can replicate in an SPF chicken lung and shows pathogenicity.

10 Claims, 7 Drawing Sheets
(2 of 7 Drawing Sheet(s) Filed in Color)

Specification includes a Sequence Listing.

CONSTRUCTION AND APPLICATION OF RECOMBINANT H5N8 SUBTYPE AVIAN INFLUENZA VIRUS CARRYING MAPPLE FLUORESCENCE REPORTER GENE

CROSS-REFERENCE TO RELATED APPLICATIONS

This application is based upon and claims the benefit of priority of the prior Chinese Patent Application No. 202310188363.1, filed Feb. 28, 2023, the entire contents of which are incorporated herein by reference.

REFERENCE TO SEQUENCE LISTING SUBMITTED ELECTRONICALLY

The present disclosure includes a sequence listing file in XML format submitted electronically, which is incorporated herein by reference in its entirety. The sequence listing file entitled "P23GZ1NW00051US.xml" was created on Dec. 23, 2025, with a file size of 8,905 bytes.

TECHNICAL FIELD

The present disclosure relates to the field of molecular biology and genetic engineering, and in particular to construction and application of a recombinant H5N8 subtype avian influenza virus carrying an mApple fluorescence reporter gene.

BACKGROUND

Avian influenza virus is a reverse strand RNA virus in Type A influenza virus, and may be classified into different subtypes according to the antigenic differences of hemagglutinin (HA) and neuraminidase (NA). There are 16 HA antigenic types and 9 NA antigenic types, and different influenza virus subtypes are formed by different HAs and NAs. The avian influenza virus subtypes identified infecting people at present include H5N1, H9N2, H7N7, H7N2, H7N3, H5N2, H5N8, H10N7 and H6N1. A novel H5N8 is the avian influenza virus subtype burst to infect people in 2013. The people who infected with H5N8 mainly have flu-like symptoms which are further developed into severe conditions such as pneumonia and acute respiratory distress syndrome. H5N8 causes severe conditions with a high proportion, with the mortality up to 29%, thereby raising wide concern in all sectors of society.

Related researches on mammalian influenza viruses are usually preformed for detecting in vitro the expression of NP proteins of the viruses in infected cells based on cell rupture by means of flow cytometry or immunofluorescence technique, or for detecting in vivo infection by means of assays such as immunocytochemistry and fluorescent slicing. These methods feature complicated steps, long consumed time and high cost, and are unable to analyze the distribution of the viruses in vivo intuitively. One of the important technical methods for virus researches is to construct an influenza virus fused with a fluorescence reporter gene by means of the reverse genetic technique. At present, various subtype influenza viruses, including H9N2, H7N9 and H1N1, carrying fluorescence reporter gene have been successfully applied to in vivo or in vitro researches. However, there have been no report yet on an H5N8 subtype recombinant virus carrying fluorescence reporter gene.

SUMMARY

The present disclosure aims to solve at least one of the technical problems existing in the prior art. In view of this, the present disclosure provides an NS protein, and a recombinant H5N8 subtype avian influenza virus containing the NS protein has weaker virulence compared with a wild H5N8 virus, and is capable of replicating in the lung of an SPF chicken and shows pathogenicity.

The present disclosure further provides a recombinant H5N8 subtype avian influenza virus carrying an mApple fluorescence reporter gene.

The present disclosure further provides a nucleic acid molecule encoding the NS protein.

The present disclosure further provides a biological material.

The present disclosure further provides a method for constructing the recombinant H5N8 subtype avian influenza virus.

The present disclosure further provides a method for constructing a poultry animal infection model based on the recombinant H5N8 subtype avian influenza virus.

The present disclosure further provides the application of the nucleic acid molecule, the biological material, the construction methods and the recombinant H5N8 subtype avian influenza virus carrying the mApple fluorescence reporter gene.

According to a first aspect of the present disclosure, an embodiment provides an NS protein comprising an amino acid sequence from positions 1 to 217 of SEQ ID NO: 2, an amino acid sequence of an mApple fluorescence reporter gene and an amino acid sequence from positions 480 to 600 of SEQ ID NO: 2 linked in order.

Specifically, the NS protein has an amino acid sequence comprising an amino acid sequence from positions 1 to 217 of SEQ ID NO: 2, an amino acid sequence of an mApple fluorescence reporter gene and an amino acid sequence from positions 480 to 600 of SEQ ID NO: 2 linked in order.

According to some embodiments of the present disclosure, the amino acid sequence of the mApple fluorescence reporter gene is as shown from positions 222 to 457 of SEQ ID NO: 2.

According to some embodiments of the present disclosure, a nucleotide sequence encoding the mApple fluorescence reporter gene is as shown from positions 711 to 1418 of SEQ ID NO: 1.

According to some embodiments of the present disclosure, the NS protein is obtained by expressing a recombinant expression vector containing the nucleotide sequence shown as SEQ ID NO: 1.

According to some embodiments of the present disclosure, the NS protein further comprises a linker peptide 1 for linking the amino acid sequence from positions 1 to 217 of SEQ ID NO: 2 to the amino acid sequence of the mApple fluorescence reporter gene; and a linker peptide 2 for linking the amino acid sequence of the mApple fluorescence reporter gene to the amino acid sequence from positions 480 to 600 of SEQ ID NO: 2.

According to some embodiments of the present disclosure, the linker peptide 1 is a non-self-cleavable peptide. Specifically, the linker peptide 1 may be a flexible linker peptide or a rigid linker peptide. Specifically, the flexible linker peptide comprises, but not limited to, GSGG (SEQ ID NO: 3). Specifically, the rigid linker peptide comprises, but not limited to, EAAAK (SEQ ID NO: 4).

According to some embodiments of the present disclosure, the linker peptide 2 is a self-cleavable peptide. Specifically, the self-cleavable peptide comprises, but not limited to, P2A, T2A, E2A, and F2A.

According to some embodiments of the present disclosure, the NS protein may further comprise a tag linked to an N terminal and/or a C terminal.

According to a second aspect of the present disclosure, an embodiment provides a recombinant H5N8 subtype avian influenza virus carrying an mApple fluorescence reporter gene having a genomic RNA composed of eight independent RNA fragments shown in 1) and 2):

1) the following 7 RNA fragments identical to those of the genomic RNA of a wild H5N8 subtype avian influenza virus: an RNA fragment 1 encoding an HA protein, an RNA fragment 2 encoding an NA protein, an RNA fragment 3 encoding an M protein, an RNA fragment 4 encoding a PA protein, an RNA fragment 5 encoding a PB1 protein, an RNA fragment 6 encoding a PB2 protein, and an RNA fragment 7 encoding an NP protein; and 2) an RNA fragment 8 encoding the NS protein according to the embodiments of the first aspect of the present disclosure.

According to some embodiments of the present disclosure, the wild H5N8 subtype avian influenza virus comprises H5N8 subtype avian influenza viral strain A/chicken/Guang-dong/JM01/2020.

According to some embodiments of the present disclosure, the amino acid sequence of the mApple fluorescence reporter gene is as shown from positions 222 to 457 of SEQ ID NO: 2.

According to some embodiments of the present disclosure, a nucleotide sequence encoding the mApple fluorescence reporter gene is as shown from positions 711 to 1418 of SEQ ID NO: 1.

According to a third aspect of the present disclosure, an embodiment provides a biological material according to any one of A1-A6:

A1: a nucleic acid molecule encoding the NS protein according to the embodiments of the first aspect of the present disclosure;

A2: an expression cassette containing the nucleic acid molecule of A1;

A3: a recombinant vector containing the nucleic acid molecule of A1;

A4: a recombinant microorganism containing the nucleic acid molecule of A1;

A5: a transgenic cell line containing the nucleic acid molecule of A1; and

A6: a recombinant virus containing the nucleic acid molecule of A1.

Specifically, a biological material comprising any one selected from the group consisting of:

A1: a nucleic acid molecule encoding the NS protein according to the embodiments of the first aspect of the present disclosure;

A2: an expression cassette containing the nucleic acid molecule of A1, a promoter and a transcription termination sequence;

A3: a recombinant vector obtained by inserting the nucleic acid molecule of A1 into an expression vector;

A4: a recombinant microorganism transfected with the nucleic acid molecule of A1;

A5: a transgenic cell line transfected with the nucleic acid molecule of A1; and A6: a recombinant virus carrying the nucleic acid molecule of A1.

According to some embodiments of the present disclosure, the nucleic acid molecule may be a DNA, such as cDNA, genomic DNA or a recombinant DNA, or an RNA, such as mRNA or hnRNA.

According to some embodiments of the present disclosure, the expression cassette refers to a DNA molecule capable of expressing a protein encoded by the nucleic acid molecule in a host cell. The expression cassette may comprise, but not limited to, a promoter and a transcription termination sequence. For example, the expression cassette may further comprise an enhancer sequence.

According to some embodiments of the present disclosure, the recombinant vector is a recombinant expression vector or a recombinant cloning vector. Specifically, the recombinant vector may be a plasmid, a cosmid, a phage or a virus vector.

According to some embodiments of the present disclosure, the recombinant microorganism may be a bacterium, a yeast, an algae or a fungus.

According to some embodiments of the present disclosure, the transgenic cell line does not include animal and plant propagating materials.

According to some embodiments of the present disclosure, the recombinant virus may be a recombinant adeno-virus or a recombinant adeno-associated virus carrying the nucleic acid molecule.

According to some embodiments of the present disclosure, the nucleic acid molecule of A1 comprises any one selected from the group consisting of:

B1: a nucleic acid molecule comprising a nucleotide sequence from positions 1 to 710 of SEQ ID NO: 1, a nucleotide sequence of the mApple fluorescence reporter gene, and a nucleotide sequence from positions 1419 to 1876 of SEQ ID NO: 1 linked in order;

B2: a nucleic acid molecule hybridized with the nucleic acid molecule of B1 and encoding the NS protein according to the embodiments of the first aspect of the present disclosure; and B3: a nucleic acid molecule having at least 90% of homology with the nucleic acid molecule of B1 or B2 and encoding the NS protein according to the embodiments of the first aspect of the present disclosure.

Specifically, the nucleic acid molecule of B1 has a nucleotide sequence comprising a nucleotide sequence from positions 1 to 710 of SEQ ID NO: 1, a nucleotide sequence of the mApple fluorescence reporter gene, and a nucleotide sequence from positions 1419 to 1876 of SEQ ID NO: 1 linked in order.

According to a fourth aspect of the present disclosure, an embodiment provides a method for constructing a recombinant H5N8 subtype avian influenza virus carrying an mApple fluorescence reporter gene, comprising:

transfecting a cell with a recombinant expression vector combination capable of expressing cDNA fragments corresponding to the eight RNA fragments according to the embodiments of the second aspect of the present disclosure; inoculating a cell liquid to a chicken embryo after culturing the cell; and culturing the chicken embryo to obtain the recombinant H5N8 subtype avian influenza virus carrying the mApple fluorescence reporter gene.

According to some embodiments of the present disclosure, the recombinant expression vector combination is a recombinant vector obtained by inserting each of genes or a plurality of genes into an expression vector, that is to say, each of genes may be either inserted into a single expression vector or divided into several groups which are respectively inserted into separate expression vectors. Each gene is distributed on each recombinant vector independently or in combination with a plurality of genes. In other word, each of recombinant vectors may express either a single gene or a plurality of coupled genes. The above each gene refers to the cDNA fragments respectively encoding the HA protein, the NA protein, the M protein, the PA protein, the PB1 protein, the PB2 protein, the NP protein or the NS protein according to the embodiments of the first aspect of the present disclosure.

According to some embodiments of the present disclosure, the cell is a host cell permitting the replication of the H5N8 subtype avian influenza virus. The cell comprises a mammalian cell.

According to some embodiments of the present disclosure, the mammalian cell is a 293T cell, a COS7 cell, an MDCK cell, a VERO cell, a WI-38 cell, an HL-8 cell, or a Hela cell.

According to some embodiments of the present disclosure, the recombinant expression vector comprises a bidirectional expression vector. The bidirectional expression vector comprises, but not limited to, a pDZ-B5 or pHW2000 vector. The bidirectional expression vectors common in the art can be applicable.

According to the embodiments of the present disclosure, the time for transfecting ranges from 4 h to 8 h. For example, the time for transfecting may be 4 h, 4.5 h, 5 h, 5.5 h, 6 h, 6.5 h, 7 h, 7.5 h, or 8 h.

According to some embodiments of the present disclosure, the cell liquid comprises at least one of a cell, a cell lysis product and a cell culture supernatant.

According to some embodiments of the present disclosure, a method for obtaining the cell liquid comprises the following steps: culturing the transfected cell with a culture medium containing pancreatin and bovine serum albumin (BSA), and freeze-thawing the cultured cell to obtain the cell liquid. The time for culturing preferably ranges from 36 h to 60 h. For example, the time for culturing may be 36 h, 40 h, 44 h, 48 h, 52 h, 56 h, or 60 h.

According to some embodiments of the present disclosure, the chicken embryo comprises a 9 to 11-day-old SPF chicken embryo.

According to a fifth aspect of the present disclosure, an embodiment provides an application of any one of C1-C4 in D1 or D2:

C1: the NS protein according to the embodiments of the first aspect of the present disclosure;

C2: the recombinant H5N8 subtype avian influenza virus carrying the mApple fluorescence reporter gene according to the embodiments of the second aspect of the present disclosure;

C3: the biological material according to the embodiments of the third aspect of the present disclosure;

C4: the construction method according to the embodiments of the fourth aspect of the present disclosure;

D1: preparation of a cell model or an animal model for screening an agent resisting an H5N8 subtype avian influenza virus; and D2: preparation of a product for researching an infection mechanism of the H5N8 subtype avian influenza virus.

Specifically, a method for preparing a cell model or an animal model for screening an agent resisting an H5N8 subtype avian influenza virus, comprising employing the NS protein according to the embodiments of the first aspect of the present disclosure.

Specifically, a method for preparing a cell model or an animal model for screening an agent resisting an H5N8 subtype avian influenza virus, comprising employing the recombinant H5N8 subtype avian influenza virus carrying the mApple fluorescence reporter gene according to the embodiments of the second aspect of the present disclosure.

Specifically, a method for preparing a cell model or an animal model for screening an agent resisting an H5N8 subtype avian influenza virus, comprising employing the biological material according to the embodiments of the third aspect of the present disclosure.

Specifically, a cell model or an animal model for screening an agent resisting an H5N8 subtype avian influenza virus, wherein the cell model or animal model comprises the recombinant H5N8 subtype avian influenza virus constructed by the method according to the embodiments of the fourth aspect of the present disclosure.

Specifically, a method for researching an infection mechanism of the H5N8 subtype avian influenza virus, comprising employing the NS protein according to the embodiments of the first aspect of the present disclosure.

Specifically, a method for researching an infection mechanism of the H5N8 subtype avian influenza virus, comprising employing the recombinant H5N8 subtype avian influenza virus carrying the mApple fluorescence reporter gene according to the embodiments of the second aspect of the present disclosure.

Specifically, a method for researching an infection mechanism of the H5N8 subtype avian influenza virus, comprising employing the biological material according to the embodiments of the third aspect of the present disclosure.

Specifically, a product for researching an infection mechanism of the H5N8 subtype avian influenza virus, wherein the product comprises the recombinant H5N8 subtype avian influenza virus constructed by the method according to the embodiments of the fourth aspect of the present disclosure.

According to some embodiments of the present disclosure, the animal model comprises a poultry animal model or a mammalian model. The poultry animal model comprises, but not limited to, a chicken, a duck, a goose and a quail. The mammalian model comprises, but not limited to, a pig and a mouse.

According to a sixth aspect of the present disclosure, an embodiment provides a method for constructing a poultry animal infection model based on the recombinant H5N8 subtype avian influenza virus, comprising:

inoculating intranasally the recombinant H5N8 subtype avian influenza virus carrying the mApple fluorescence reporter gene according to the embodiments of the second aspect of the present disclosure into a poultry animal, to obtain the poultry animal infection model. The poultry animal infection model may be observed by an in vivo imaging instrument.

According to some embodiments of the present disclosure, the poultry animal comprises, but not limited to, a chicken, a duck, a goose and a quail. The poultry animal may be a poultry animal at SPF level.

According to some embodiments of the present disclosure, the poultry animal is a chicken, and an inoculating effective dose of the recombinant H5N8 subtype avian influenza virus carrying the mApple fluorescence reporter gene is $10^3$ to $10^6$ $EID_{50}$. The poultry animal is preferably a 3-week-old chicken.

According to the embodiments of the present disclosure, the infection time is 2 to 14 days. For example, the infection time may be 2 days, 3 days, 4 days, 5 days, 6 days, 7 days, 8 days, 9 days, 10 days, 11 days, 12 days, 13 days or 14 days.

The present disclosure at least has the following beneficial effects:

1. H5N8 virus is a highly pathogenic avian influenza virus. In the process of constructing a recombinant virus, due to the high pathogenicity, the chicken embryo is easily lethal in an adaptive passage operation for virus rescue and would be dead within 24 h, making it is difficult to collect the passaged virus. The present disclosure has constructed a recombinant H5N8 subtype avian influenza virus which, compared with a wild H5N8 virus, has a weakened virulence, and is able to replicate in the lung of an SPF chicken and shows pathogenicity. After passage through the SPF chicken embryo, the recombinant H5N8 subtype avian influenza virus maintains the pathogenicity and luminescent property, having a good stability.

2. Compared with mouse, chicken has the tissue and feather which may interfere with the imaging sensitivity and specificity due to autofluorescence. Compared with other luciferases, mApple, a red fluorescence protein possesses better penetrability and a higher brightness in media, and a low intracellular imaging background. A substrate does not need to take part in a catalytic reaction for the luminescence, and thus the mApple is appropriate for research on in vivo and in vitro infections and capable of avoiding interference caused by the autofluorescence of the tissue and feather of the chicken, thereby facilitating in vivo imaging observation. A poultry animal infection model (including a chicken infection model) constructed with the recombinant H5N8 subtype avian influenza virus carrying the mApple fluorescence reporter gene can be analyzed visibly, that is, without dissection, the distribution positions and infection trend of the recombinant H5N8 subtype avian influenza virus in vivo can be detect by means of whole organ imaging and flow cytometry, and further the virus load can also be rapidly evaluated. Therefore, a visual tool is established for researching avian influenza virus, which is also of great significance for the researches on the transmissibility, pathogenicity and pathogenic mechanism of the avian influenza virus.

Further characteristics and advantages of the embodiments of the present disclosure will be set forth in the following description, and become apparent from the description partially or can be understood by implementing the embodiments of the present disclosure.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
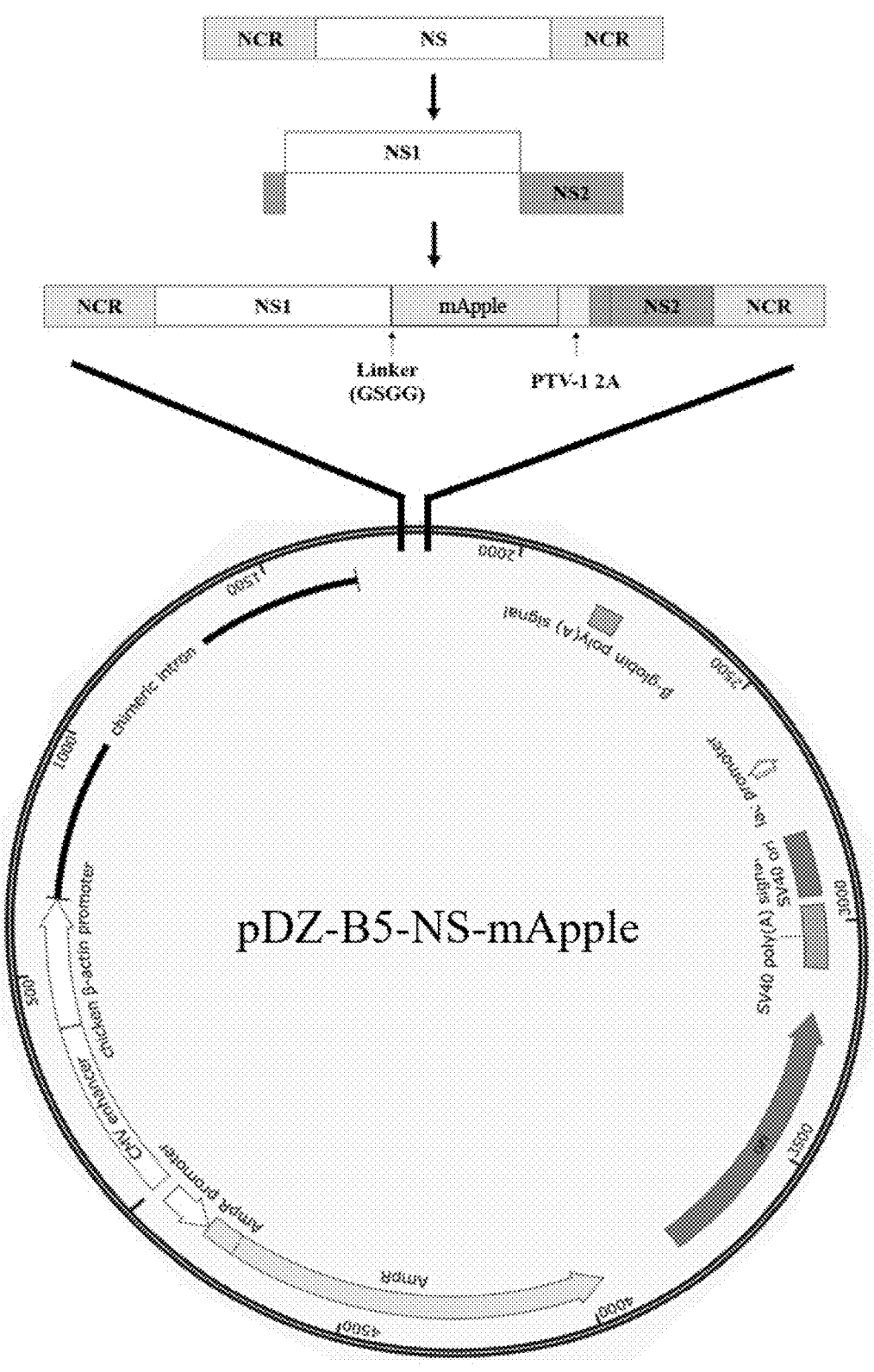
FIG. 1 is a schematic diagram for constructing a recombinant plasmid pDZ-B5-NS-mApple in an embodiment of the present disclosure.

The concept and the technical effect of the present disclosure will be clearly and intactly described hereafter with reference to exemplary implementations, for the convenience of full understanding the purpose, the features and the effects of the present disclosure. Apparently, the described embodiments are merely a part of, rather than all of the embodiments of the present disclosure. Based on the implementations of the present disclosure, other implementations obtained by those skilled in the art without making creative efforts shall fall within the protection scope of the present disclosure.

Embodiments with unmarked specific conditions below generally follow conventional conditions, for example, see Sambrook J & Russell D W, Molecular Cloning: a Laboratory Manual, 2001, or conditions recommended by manufacturers. The reagents or instruments which are not indicated with manufacturers are conventional products which are available on market.

Throughout the description of the present disclosure, the terms "comprise" and "have" and any deformation thereof are intended to cover non-exclusive inclusions, for example, a process, method, system, product or device which comprise a series of steps or elements have not to be limited to these steps or elements clearly listed but to include other steps or elements that are not listed clearly and other inherent steps or elements for the process, method, product or device.

A bidirectional expression vector pDZ-B5, a 293T cell line and an MDCK cell involved in the present disclosure are stored in Zoonose Prevention and Control Preparation National and Local Joint Engineering Laboratory.

9 to 11-day-old chicken embryos were purchased from Xinxing Dahua Agricultural Egg Co., Ltd., Guangdong. SPF chickens were purchased from Xinxing Dahua Agricultural Egg Co., Ltd., Guangdong.

Plasmids pDZ-B5-HA, pDZ-B5-NA, pDZ-B5-M, pDZ-B5-PA, pDZ-B5-PB1, pDZ-B5-PB2 and pDZ-B5-NP involved in the present disclosure all were constructed based on a pDZ-B5 plasmid as a starting plasmid, wherein the plasmid pDZ-B5-HA was constructed by inserting cDNA of an HA gene (GenBank: OP748410) of an H5N8 avian influenza virus strain A/chicken/Guangdong/JM01/2020 (hereinafter referred to as a wild H5N8 virus) at the site BsmB I of a plasmid pDZ-B5 (specifically, the cDNA was amplified with a specific primer containing homologous arms (i.e., having partial sequences of a pDZ-B5 vector) upstream and downstream, and then the amplified cDNA of the HA gene with the homologous arms was linked to the plasmid pDZ-B5 through homologous recombination; similarly hereinafter);

the plasmid pDZ-B5-NA was constructed by inserting cDNA of an NA gene (GenBank: OP748414) of the H5N8 virus at the site BsmB I of the plasmid pDZ-B5;

the plasmid pDZ-B5-M was constructed by inserting cDNA of an M gene (GenBank: OP748415) of the H5N8 virus at the site BsmB I of the plasmid pDZ-B5;

the plasmid pDZ-B5-PA was constructed by inserting cDNA of a PA gene (GenBank: OP748417) of the H5N8 virus at the site BsmB I of the plasmid pDZ-B5;

the plasmid pDZ-B5-PB1 was constructed by inserting cDNA of a PB1 gene (GenBank: OP748412) of the H5N8 virus at the site BsmB I of the plasmid pDZ-B5;

the plasmid pDZ-B5-PB2 was constructed by inserting cDNA of a PB2 gene (GenBank: OP748411) of the H5N8 virus at the site BsmB I of the plasmid pDZ-B5; and the plasmid pDZ-B5-NP was constructed by inserting cDNA of an NP gene (GenBank: OP748413) of the H5N8 virus at the site BsmB I of the plasmid pDZ-B5.

Construction of Recombinant NS Gene Plasmid pDZ-B5-NS-mApple

The schematic diagram for construction of the recombinant plasmid pDZ-B5-NS-mApple is shown in FIG. 1.

The sequence of NS-mApple fragment is shown as SEQ ID NO: 1, including: a head protective base and recognition site of a restriction enzyme BsmBI (sites 1 to 21), a sequence of a noncoding region at the 3' terminal of an NS segment of the virus (sites 22 to 47), a sequence of a coding region of an NS1 segment of the virus (without terminator) (sites 48 to 698), a Linker (GSGG) sequence (SEQ ID NO: 3) (sites 699 to 710), a sequence of the mApple fluorescence reporter gene (without terminator) (sites 711 to 1418), a coding sequence of a 2A peptide segment of a PTV-1 virus (sites 1419 to 1484), a sequence of a coding region of an NEP segment of the virus (sites 1485 to 1850), a sequence of a noncoding region at the 5' terminal of the NS segment of the virus (sites 1851 to 1876) and a terminal protective base and recognition site of the restriction enzyme BsmBI (sites 1877 to 1897). Conformed by sequencing, NS-mApple was then linked to the plasmid pDZ-B5 digested by BsmB I (purchased from NEB) through a homologous recombinant kit (One Step Cloning Kit, purchased from Vazyme), to obtain the recombinant plasmid pDZ-B5-NS-mApple.

```
The NS-mApple fragment (SEQ ID NO. 1):
CGACCTCCGAAGTTGGGGGGGAGCAAAAGCAGGGTGACAAAAACATAATG

GATACCAACACTATGCTAAGCTTTCAGGTAGACTGTTTTCTTTGGTATGT

CCGCAAACGATTCGCAGACCAAGAACTGGGTGATGCCCCTTTCCTTGACC

GGCTTCGCCGAGATCAGAAGTCTTTAAGAGGAAGAGGCACCACTCTTGGT

CTGAGCATCGAAGCAGCTACTCGTGAGGGAAAGCAGATAGTGAAGCGAAT

TCTGAAGGAAGAGTCTGATGAGGCACTTAAAATGACTGTTGCTTCAGGTC

CGTCTTCACGCTACCTAACTGATATGACTCTTGAAGAGATGTCAAGGGAC

TGGTTCATGCTCATGCCCAAACGGAAAGTGGCAGGTCCACTTTGCATCAA

AATGGACCAGGCAATAATGGATAAAAACATCATATTGAAAGCAAACTTCA

GTGTAATTTTCAACCGGCTGGAAGCTCTAATACTACTTCGAGCTTTCACA

GAAGAAGGAGCAATTGTGGGAGAAATCTCACCGTTACCTTCTTTTCCAGG

ACATACTGATGAGGATGTCAAAAATGCAATTGGGGTCCTCATCGGAGGGC

TTGAATGGAATAATAACACAGTTCGGGTCTCTGAAACTCTACAGAGATTC

GCTTGGAGAAACAGTGATGAGGATGGGAGACCTTCACTCCCTCCAAAGGG

ATCCGGTGGAATGGTGAGCAAGGGCGAGGAGAATAACATGGCCATCATCA

AGGAGTTCATGCGCTTCAAGGTGCACATGGAGGGCTCCGTGAACGGCCAC
```

-continued
```
GAGTTCGAGATCGAGGGCGAGGGCGAGGGCCGCCCCTACGAGGCCTTTCA

GACCGCTAAGCTGAAGGTGACCAAGGGTGGCCCCCTGCCCTTCGCCTGGG

ACATCCTGTCCCCTCAGTTCATGTACGGCTCCAAGGTCTACATTAAGCAC

CCAGCCGACATCCCCGACTACTTCAAGCTGTCCTTCCCCGAGGGCTTCAG

GTGGGAGCGCGTGATGAACTTCGAGGACGGCGGCATTATTCACGTTAACC

AGGACTCCTCCCTGCAGGACGGCGTGTTCATCTACAAGGTGAAGCTGCGC

GGCACCAACTTCCCCTCCGACGGCCCCGTAATGCAGAAGAAGACCATGGG

CTGGGAGGCCTCCGAGGAGCGGATGTACCCCGAGGACGGCGCCCTGAAGA

GCGAGATCAAGAAGAGGCTGAAGCTGAAGGACGGCGGCCACTACGCCGCC

GAGGTCAAGACCACCTACAAGGCCAAGAAGCCCGTGCAGCTGCCCGGCGC

CTACATCGTCGACATCAAGTTGGACATCGTGTCCCACAACGAGGACTACA

CCATCGTGGAACAGTACGAACGCGCCGAGGGCCGCCACTCCACCGGCGGC

ATGGACGAGCTGTACAAGGGATCCGGCGCCACCAACTTCAGCCTGCTGAA

GCAGGCCGGCGACGTGGAGGAGAACCCCGGCCCCATGGATACCAACACTA

TGCTAAGTTTCCAGGACATACTGATGAGGATGTCAAAAATGCAATTGGGG

TCCTCATCGGAGGGCTTGAATGGAATAATAACACAGTTCGGGTCTCTGAA

ACTCTACAGAGATTCGCTTGGAGAAACAGTGATGAGGATGGGAGACCTTC

ACTCCCTCCAAAGTAGAAACGGAAAATGGCGAGAACAATTGGGTCAGAAG

TTTGAAGAAATAAGATGGCTGATTGAAGAAGTGCGACATAGACTGAAGAT

TACAGAAAATAGCTTCGAACAGATAACGTTTATGCAAGCCTTACAACTAT

TGCTTGAAGTGGAACAAGAGATAAGAACTTTCTCGTTTCAGCTTATTTGA

TGATAAAAAACACCCTTGTTTCTACTAATAACCCGGCGGCCCAAAAT.
```

The amino acid sequence of NS-mApple protein is shown as SEQ ID NO. 2:
```
MDTNTMLSFQVDCFLWYVRKRFADQELGDAPFLDRLRRDQKSLRGRGTTL

GLSIEAATREGKQIVKRILKEESDEALKMTVASGPSSRYLTDMTLEEMSR

DWFMLMPKRKVAGPLCIKMDQAIMDKNIILKANFSVIFNRLEALILLRAF

TEEGAIVGEISPLPSFPGHTDEDVKNAIGVLIGGLEWNNNTVRVSETLQR

FAWRNSDEDGRPSLPPKGSGGMVSKGEENNMAIIKEFMRFKVHMEGSVNG

HEFEIEGEGEGRPYEAFQTAKLKVTKGGPLPFAWDILSPQFMYGSKVYIK

HPADIPDYFKLSFPEGFRWERVMNFEDGGIIHVNQDSSLQDGVFIYKVKL

RGTNFPSDGPVMQKKTMGWEASEERMYPEDGALKSEIKKRLKLKDGGHYA

AEVKTTYKAKKPVQLPGAYIVDIKLDIVSHNEDYTIVEQYERAEGRHSTG

GMDELYKGSGATNFSLLKQAGDVEENPGPMDTNTMLSFQDILMRMSKMQL

GSSSEGLNGIITQFGSLKLYRDSLGETVMRMGDLHSLQSRNGKWREQLGQ

KFEEIRWLIEEVRHRLKITENSFEQITFMQALQLLLEVEQEIRTFSFQL

I.
```

Construction of Recombinant H5N8-mApple Virus

The recombinant H5N8 subtype avian influenza virus H5N8-mApple carrying the mApple fluorescence reporter gene was rescued by means of the reverse genetic technique. The process steps are as follows:

A 293T cell was paved in a 6-well plate coated with polylysine, and cultured with a DMEM medium (purchased from Gibco) containing 10% fetal calf serum (purchased from Gibco) till a cell density was 80-90%. Eight plasmids pDZ-B5-HA, pDZ-B5-NA, pDZ-B5-M, pDZ-B5-PA, pDZ-B5-PB1, pDZ-B5-PB2, pDZ-B5-NP and pDZ-B5-NS-mApple carrying the mApple fluorescence reporter gene, which were required for an influenza reverse genetics system, were co-transfected to the 6-well plate; and a culture solution was abandoned after transfection for 6 h, and replaced by an Opti-MEM medium containing 0.35 μg/ml TPCK pancreatin and having a final concentration of 0.2% BSA. After culture for 48 h, a resultant was repeatedly freeze-thawed for three times to collect a cell liquid, and the cell liquid was inoculated to the 9 to 11-day-old chicken embryos. After 48 h, HA positive allantoic fluids of the chicken embryos were collected, thus obtaining the recombinant H5N8-mApple virus.

Passage of Recombinant H5N8-mApple Virus

The HA positive allantoic fluids (i.e. the H5N8-mApple recombinant virus), obtained by the above method, of the chicken embryos were diluted with PBS by 1000 times; 200 μL of the diluted allantoic fluids were inoculated to the 9 to 11-day-old SPF chicken embryos; after incubating at 37° C. for 48 h, the HA positive allantoic fluids of the chicken embryos were collected and stored in a −80° C. refrigerator; and the above operations was repeated for four times.

The recombinant H5N8-mApple virus firstly obtained from the HA positive allantoic fluids of the chicken embryos was specified as the P1 generation, and the recombinant H5N8-mApple virus passaged through the 9 to 11-day-old SPF chicken embryos were named as P2-P4 generations in sequence.

Identification of Recombinant H5N8-mApple Virus (1) Identification of mApple Fluorescence Reporter Gene Total RNA of the recombinant H5N8-mApple viruses of the P1-P4 generations obtained above were extracted by using an RNA rapid extraction kit (purchased from Shanghai Feijie Co. Ltd.), and subjected to reverse transcription by using random primers to obtain cDNA. After PCR amplification with specific primers (mApple-F and mApple-R) for the mApple fluorescence reporter gene and taking the wild H5N8 virus as a control (labeled as WT), the amplified product was sent to Sango Biotech for sequencing to, in combination with electrophoresis, determine the presence of the mApple fluorescence reporter gene.

Nucleotide sequences of the mApple-F and Apple-R are as follows:

```
                                        (SEQ ID NO: 5)
    mApple-F:
    AAGGGATCCGGTGGAATGGTGAGCAAGGG;

(SEQ ID NO: 6)
    mApple-R:
    TGAAGTTGGTGGCGCCGGATCCCTTGTACAGCTCG.
```

Figure 2:
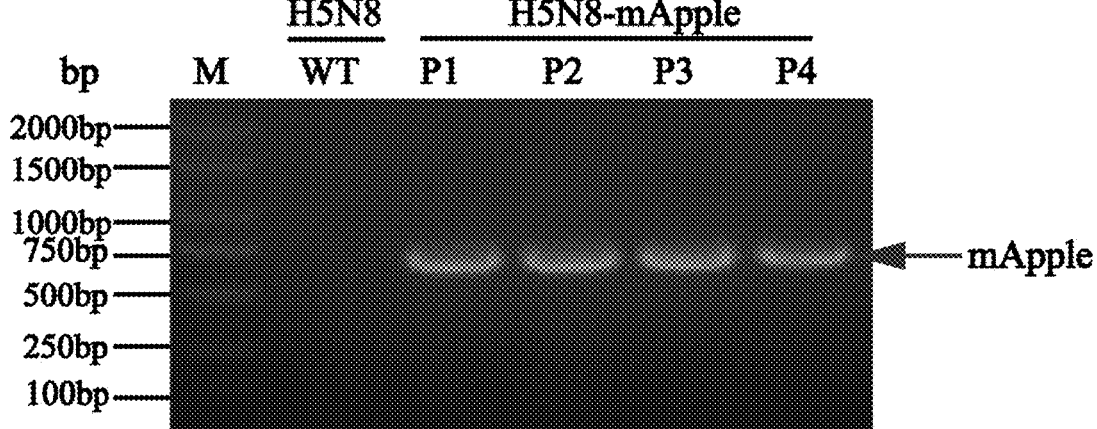
FIG. 2 is an electrophoretogram for identifying mApple gene of P1-P4 generations of a recombinant H5N8-mApple virus in an embodiment of the present disclosure.

The identification result is as shown in FIG. 2.

Confirmed by sequencing, all the constructed recombinant H5N8-mApple viruses of the P1-P4 generations contain the mApple fluorescence reporter gene, which indicates that the constructed recombinant H5N8-mApple viruses possess a stability and are able to passage stably.

(2) Western-Blot Assay on Recombinant H5N8-mApple Virus

MDCK cell was infected with the recombinant H5N8-mApple virus at MOI of 1.0, and incubated in a 37° C. incubator for 1 h, and a viral liquid was abandoned and replaced with a DMEM maintenance medium containing 0.25 μg/mL TPCK pancreatin and having a final concentration of 0.1% BSA. After infection for 12 h, the liquid in wells was abandoned, and 500 µL of a RIPA lysis buffer was added to treat the cell; a protein sample was collected, and added with a 5×SDS sampling buffer for boiling for 10 min; the denatured sample subjected to SDS-PAGE (with a 10% colloid) was transferred to a nitrocellulose membrane; 5% skim milk powder was added for blocking for 1 h; the membrane was washed with TBST for 3 times, and incubated respectively with a rabbit anti-NS1 protein antibody (purchased from Thermo) and a mouse anti-GAPDH protein antibody (purchased from Abbkine) overnight at 4° C.; then the membrane was washed with TBST for 3 times and respectively incubated with a goat anti-rabbit second antibody (purchased from TransGen Biotech) treated with HRP and a goat anti-mouse secondary antibody (purchased from Abbkine) at room temperature for 1 h; and the membrane was washed with TBST for 3 times, treated lucifugally with an HRP developing solution (purchased from Millipore), and imaged by an infrared imaging system. The wild H5N8 virus was used as a control (labeled as WT).

Figure 3:
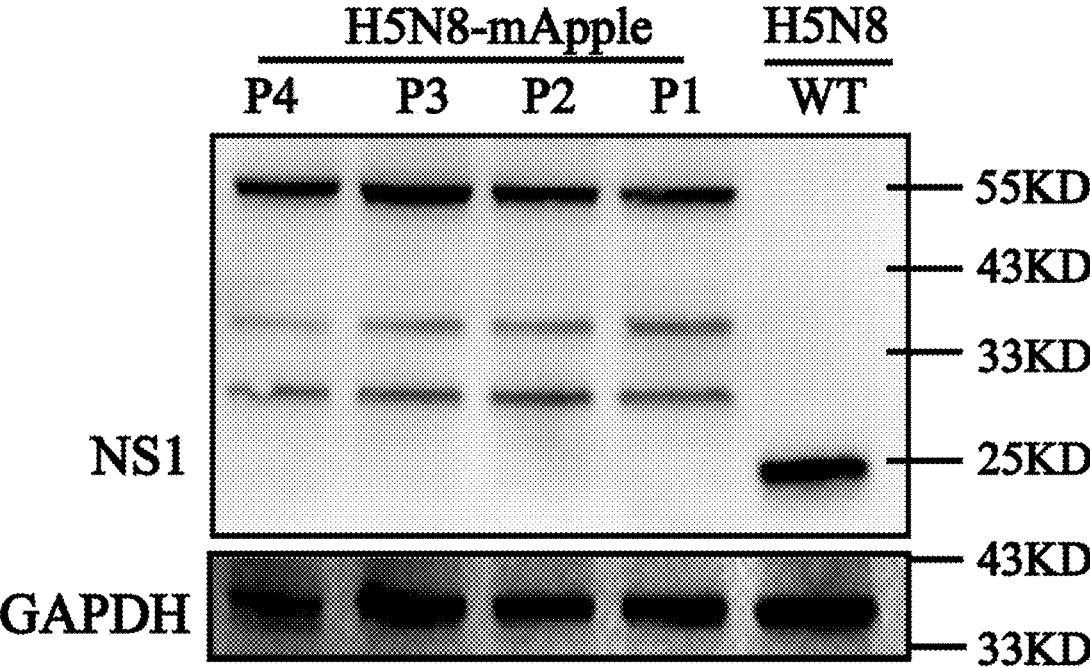
FIG. 3 is a diagram showing a Western-Blot assay result for NS1 protein of P1-P4 generations of a recombinant H5N8-mApple virus and a wild H5N8 virus and GAPDH protein in an embodiment of the present disclosure.

The assay result is shown in FIG. 3.

After the MDCK cells are infected with the recombinant H5N8-mApple virus and the wild H5N8 virus, the NS1 protein is capable of expressing normally, and the NS1 protein and the mApple fluorescence reporter protein in the recombinant H5N8-mApple virus are expressed in form of a fusion protein.

Growth Kinetics Analysis on Recombinant H5N8-mApple Virus in MDCK Cells (1) Detection of Tissue Culture Median Infective Dose ($TCID_{50}$)

MDCK cells were paved in a 96-well plate. The MDCK cells in good growth state in the 96-well plate were infected with the recombinant H5N8-mApple virus liquid (the P1 generation) at dilution of $10^{-4}$-$10^{-9}$. A blank medium without inoculating the virus was used as a negative control. After incubation in a 37° C. incubator for 1 h, the cells were washed with PBS twice, replaced and treated with a DMEM medium containing 0.25 µg/ml TPCK pancreatin and having a final concentration of 0.2% BSA, and incubated in a 37° C. incubator for 48 h to collect a supernatant for hemagglutination titer assay; and $TCID_{50}$ was calculated according to Reed-Muench method.

Cell wells inoculated at dilution of $10^{-4}$ all had lesions (8/8); six cell wells inoculated at dilution of $10^{-5}$ had lesions (6/8); two cell wells inoculated at dilution of $10^{-6}$ had lesions (2/8); and the cell wells inoculated at dilution of $10^{-7}$ to $10^{-9}$ were free of lesions. Calculated by the Reed-Muench method, the $TCID_{50}$ of the recombinant H5N8-mApple virus of the P1 generation is $10^{-5.5}$/0.1 mL.

(2) Detection of Growth Curve

The MDCK cells growing well in a 12-well plate were infected with the recombinant H5N8-mApple virus of the P1 generation at 37° C. with different MOIs (MOI=0.1, MOI=0.01, and MOI=0.001), incubated in a 37° C. incubator for 1 h, washed with PBS twice, and replaced and treated with a DMEM medium containing 0.25 µg/ml TPCK pancreatin and having a final concentration of 0.2% BSA; and the culture supernatants were collected at hour 12, hour 24, hour 36, hour 48, hour 60 and hour 72 respectively. A growth curve of the recombinant virus on the MDCK cell was measured by the $TCID_{50}$ method, with the wild H5N8 virus as a control.

Figure 4:
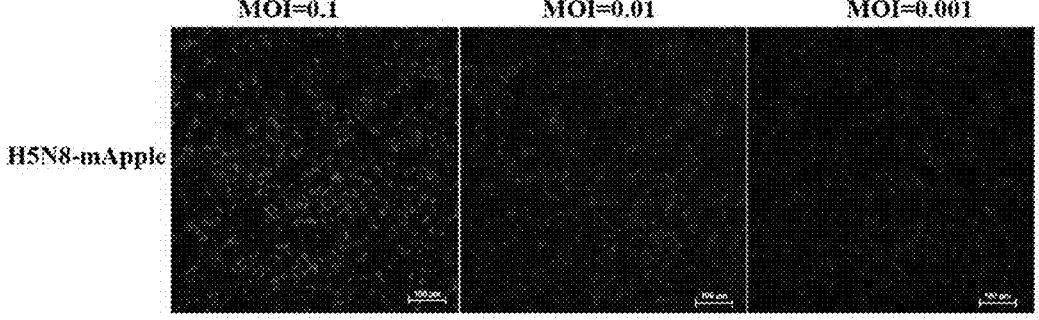
FIG. 4 is a diagram showing a fluorescence detection result for a MDCK cell infected with a recombinant H5N8-mApple virus at different multiplicities of infection (MOI) in an embodiment of the present disclosure.
Figure 5:
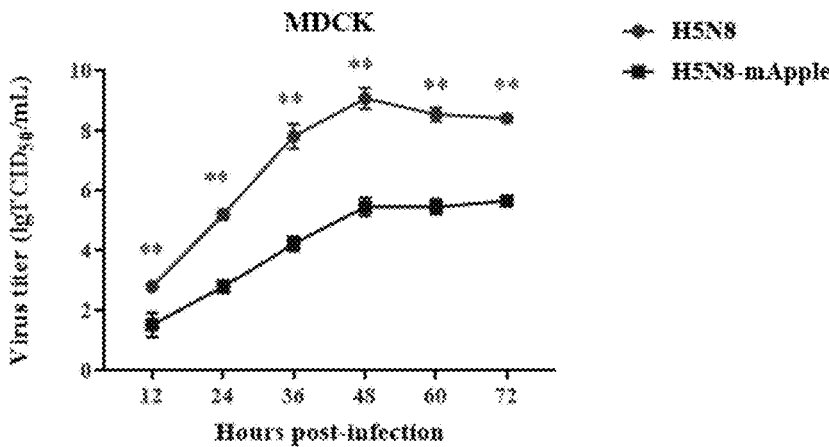
FIG. 5 is a proliferation curve graph for a recombinant H5N8-mApple virus in an MDCK cell in an embodiment of the present disclosure, wherein the recombinant H5N8-mApple virus is labeled as H5N8-mApple, and a wild H5N8 virus is labeled as H5N8.

The detection results are shown in FIG. 4 and FIG. 5.

Compared with the parent wild H5N8 virus, the replication of the recombinant H5N8-mApple virus in the MDCK cells is weakened. As shown in MDCK cells infected at different MOIs, the greater the MOI is, the higher the fluorescence intensity of mApple is (see FIG. 4); and the recombinant H5N8-mApple virus and the parent wild H5N8 virus have a significant difference in growth kinetics in the MDCK cells (see FIG. 5).

Virus Loads of SPF Chickens Infected with Recombinant H5N8-mApple Virus at Different Median Infective Doses ($EID_{50}$) of Chicken Embryos and In Vivo Imaging The experimental method is as follows:

The virus liquid was diluted into $10^3$ $EID_{50}$, $10^4$ $EID_{50}$, $10^5$ $EID_{50}$ or $10^6$ $EID_{50}$ of the recombinant H5N8-mApple virus per 200 µL PBS; 3-week-old SPF chickens were infected with 200 µL of diluted recombinant H5N8-mApple virus liquid (the P1 generation) through nasal inhalation as an H5N8-mApple group; 3-week-old SPF chickens were infected with $10^4$ $EID_{50}$/200 µL of wild H5N8 virus through nasal inhalation as an H5N8 group; and 3-week-old SPF chickens were infected with 200 µL of PBS solution through nasal inhalation as a control group. Survival conditions of three groups of SPF chickens were monitored every day. Oropharyngeal swabs and cloacal swabs of the SFP chickens in each group were collected on Day 2 to Day 4 after infection, and the virus titers in the swabs were determined by inoculating to 9 to 11-day-old chicken embryos and the $EID_{50}$ method. The virus loads in the brains, lungs and tracheas of the chickens were measured on Day 3 after infection. The SPF chickens in different groups and the lungs thereof were respectively imaged on Day 3, Day 5 and Day 7 after infection with an IVIS Lumina LT (Series III) in vivo imaging instrument.

Figure 6:
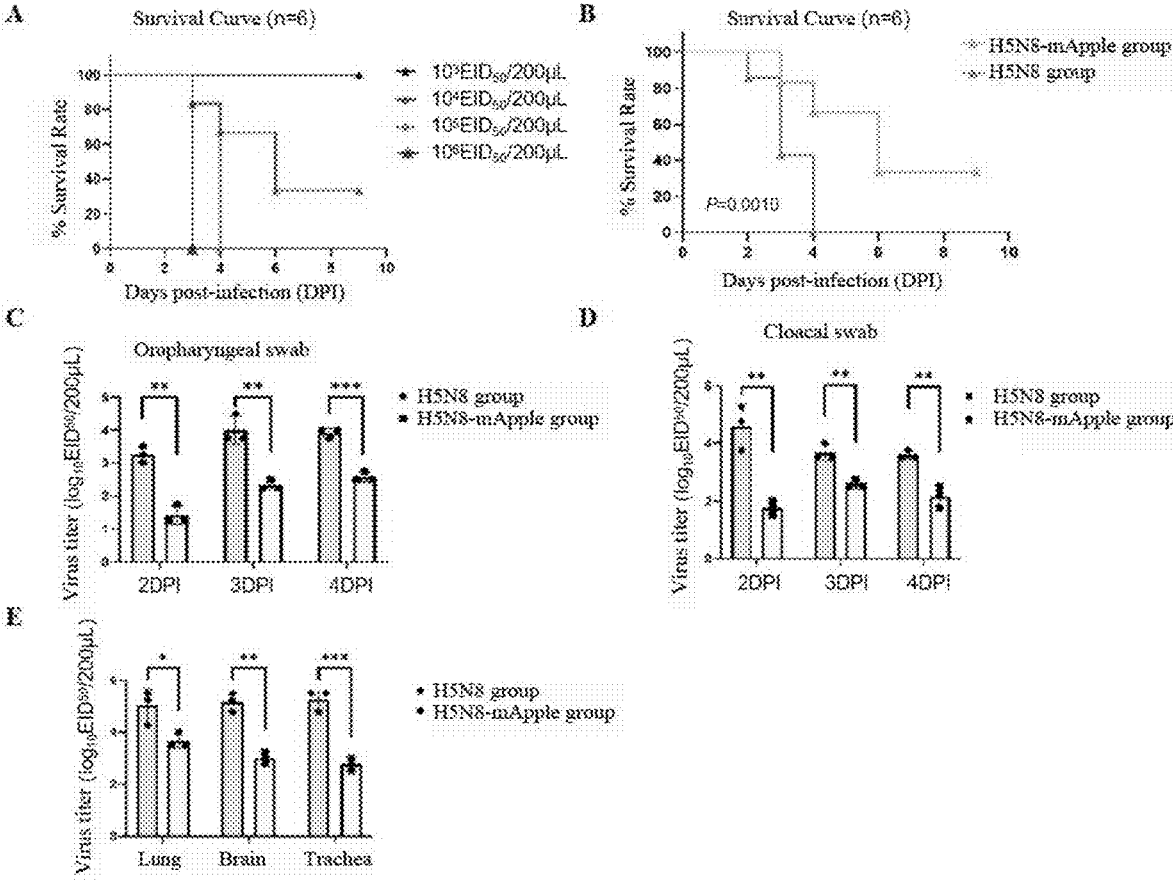
FIG. 6 is a comparative result diagram for pathogenicity of a recombinant H5N8-mApple virus and a wild H5N8 virus on an SFP chicken (a specific pathogen free chicken) in an embodiment of the present disclosure, wherein panel A is a survival rate diagram of the SFP chicken infected with the recombinant H5N8-mApple virus; panel B is a survival rate comparative diagram of the SFP chickens infected with the recombinant virus and the wild virus at an infective dose of $10^4$ $EID_{50}$/200 µL; panel C is a comparative diagram of virus titers of oropharyngeal swabs 2-4 days after the SPF chickens are infected with the recombinant virus and the wild virus; panel D is a comparative diagram of virus titers of cloacal swabs 2-4 days after the SPF chicken are infected with the recombinant virus and the wild virus; and panel E is a comparative diagram of virus titers of brains, lungs and tracheas at Day 3 after the SPF chickens are infected with the recombinant virus and the wild virus.
Figure 7:
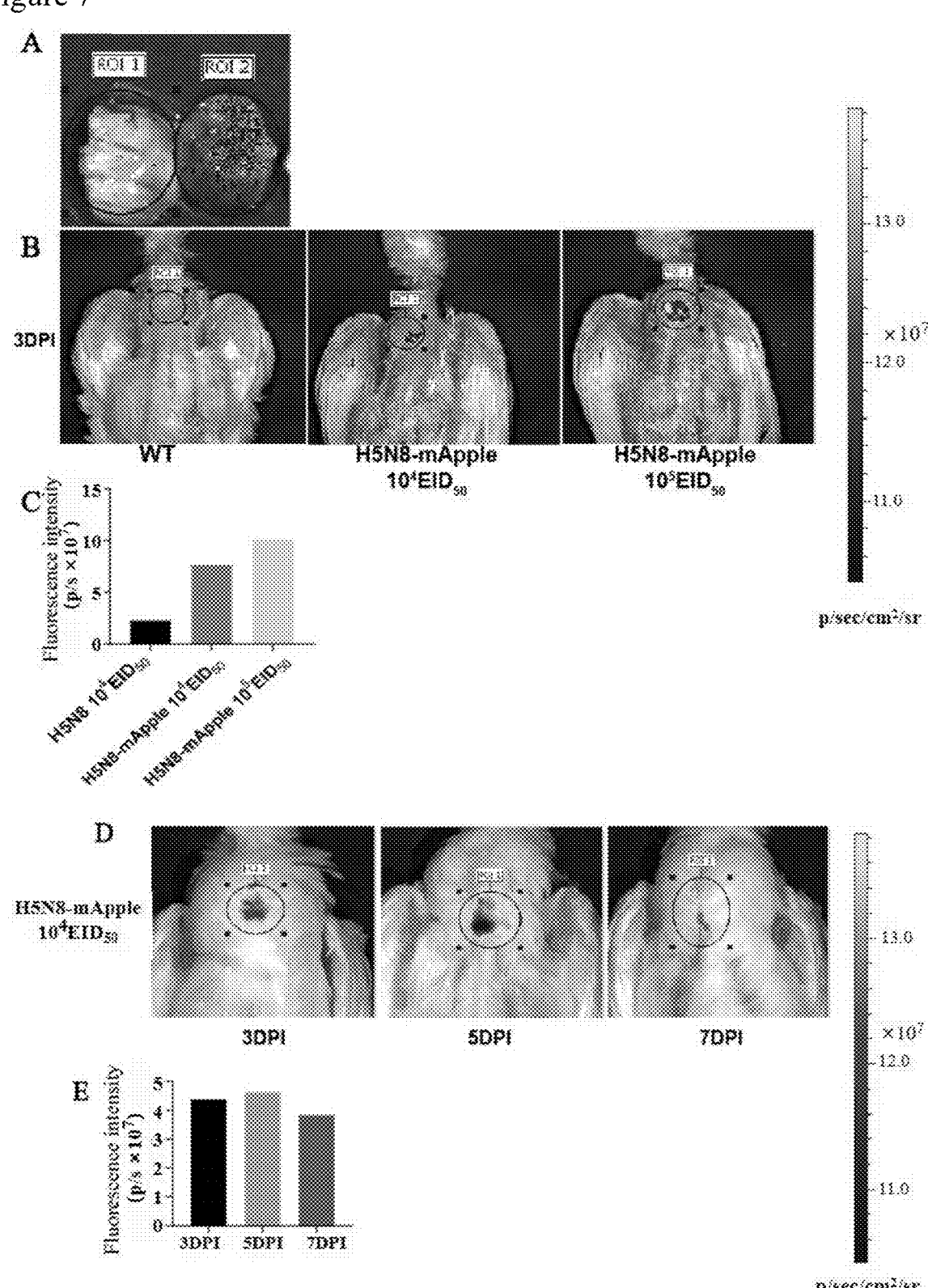
FIG. 7 is an in vivo imaging diagram for the SPF chickens infected with a recombinant H5N8-mApple virus at an infective dose of $10^4$ $EID_{50}$/200 µL in an embodiment of the present disclosure, wherein panel A left shows an imaging diagram of a lung of the SPF chicken infected with a wild virus at the infective dose of $10^4$ $EID_{50}$/200 µL on Day 3; panel A right shows an imaging diagram of a lung of the SPF chicken infected with the recombinant H5N8-mApple virus at the infective dose of $10^4$ $EID_{50}$/200 µL on Day 3; panel B shows 3 DPI fluorescence signal distribution in the SPF chicken infected with the recombinant H5N8-mApple virus at different infective doses of $EID_{50}$/200 µL; panel C is a diagram of fluorescence intensities converted from the fluorescence signals in the SPF chickens infected with the recombinant H5N8-mApple virus at different infective doses of $EID_{50}$/200 µL and the wild virus; panel D shows the fluorescence signal distribution in the SPF chicken infected with the recombinant H5N8-mApple virus at the infective dose of $10^4$ $EID_{50}$/200 µL on Day 3, Day 5 and Day 7; and panel E is a diagram of fluorescence intensities converted from the fluorescence signals in the SPF chickens infected with the recombinant H5N8-mApple virus at the infective dose of $10^4$ $EID_{50}$/200 µL and the wild virus on Day 3, Day 5 and Day 7.

The detection results are shown in FIG. 6 and FIG. 7.

Compared with the wild H5N8 virus, the recombinant H5N8-mApple virus has a reduced pathogenicity. At a challenge dose of $10^5$ $EID_{50}$/200 µL, a mortality on Day 3 was 20%, and all the chickens were dead on Day 4. At a challenge dose of $10^6$ $EID_{50}$/200 µL, all the chickens were dead on Day 3. The recombinant H5N8-mApple virus is able to replicate efficiently in lung, brain and trachea (particularly, in the lung), but the virus titer is lower than that of the wild H5N8 virus. The results are shown in FIG. 6.

The recombinant H5N8-mApple virus can replicate efficiently in the lung and shows fluorescence. The fluorescence intensities in the lungs are increased with the increase of the challenge dose of the recombinant mApple-H5N8 virus. At the same dose of the recombinant mApple-H5N8 virus, the fluorescence intensity detected on Day 5 after infection to the SPF chicken is higher than those on Day 3 and Day 7. The results are shown in FIG. 7.

Infection of Immune Cells in Lungs of SPF Chickens with Recombinant H5N8-mApple Virus The experimental method is as follows:

The recombinant H5N8-mApple virus liquid (the P1 generation) was diluted into $10^4$ $EID_{50}$ of the recombinant H5N8-mApple virus per 200 µL PBS; 3-week-old SPF chickens were infected through nasal inhalation, the chicken lungs were digested and separated on Day 3 and Day 5 after infection to obtain cell suspensions. The cells ($1×10^6$) were incubated lucifugally with an APC labeled CD45 antibody (purchased from SouthernBiotech) for 30 min. After washing with PBS, the stained cells were analyzed with a flow cytometer (purchased from Beckman Coulter), identified as an infection group. A single-cell suspension from SPF chicken lung and treated with PBS was stained in the same way, identified as a control group.

Figure 8:
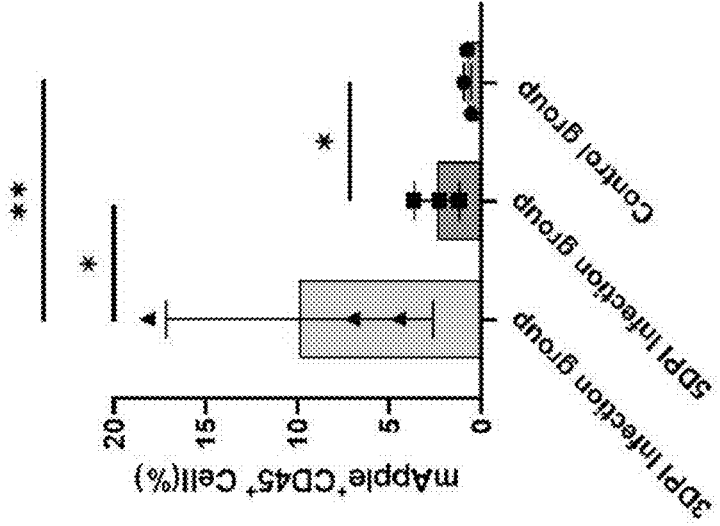
FIG. 8 is a variation diagram for infected immune cells ($mApple^+CD45^+$) from lungs of an SPF chickens infected with an recombinant H5N8-mApple virus at an infective dose of $10^4$ $EID_{50}$/200 µL on Day 3 and Day 5 in an embodiment of the present disclosure, wherein the upper diagram shows a contour plot for the infected immune cells ($mApple^+CD45^+$) of three chickens from an H5N8-mApple infection group and a control group on Day 3 and Day 5; and the lower diagram shows a variation diagram of the infected immune cells ($mApple^+CD45^+$) on Day 3 and Day 5.
Figure 8:
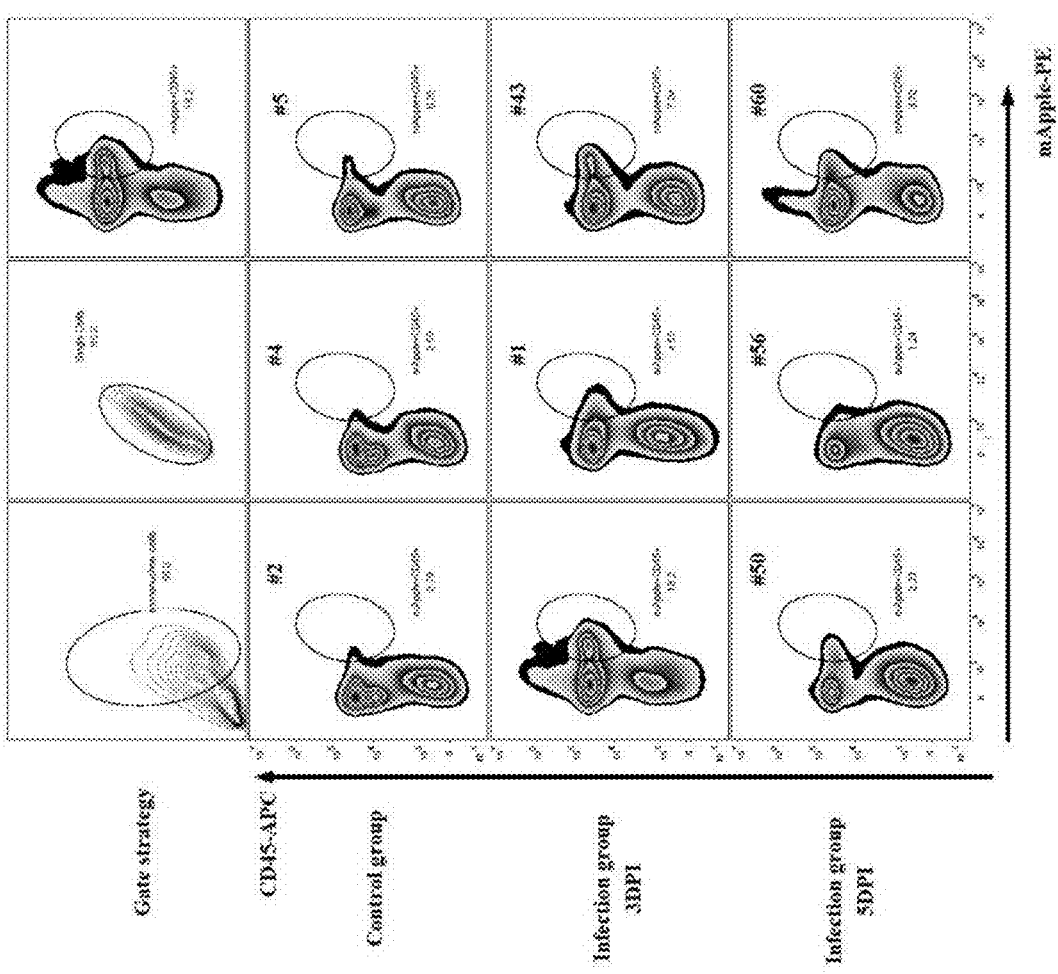

The detection test results are shown in FIG. 8.

On Day 3 after the SPF chickens are infected with the H5N8-mApple recombinant virus, a significant expression of the fluorescent protein mApple of the recombinant virus was detected in the lung immune cells, and a proportion of the infected immune cells is 4.55%-18.2% (CD45$^+$ mApple$^+$), compared to 0.58%-0.95% of the control group. In addition, the immune cells infected with the recombinant virus can still be detected (1.24%-3.7%) on Day 5 after infection, but the significance is reduced compared with on Day 3 (P<0.05).

In Vitro Infection of PBMCs with Recombinant H5N8-mApple Virus

The experimental method is as follows:

Cervical venous blood of the SPF chickens was collected and separated into peripheral blood mononuclear cell (PBMC) suspension with a chicken peripheral blood lymphocyte separation kit (purchased from Tianjin Haoyang Biological Manufacture Co., Ltd.), and the cell suspension was mixed with 0.08% trypan blue at a ratio of 1:1 for counting. The PBMCs of a cell quantity being 2×10$^6$ were infected with the recombinant mApple-H5N8 viruses at MOIs of 5, 10 and 15 respectively, and incubated at 39° C. for 1 h, where a tube wall were flipped lightly for a full contact of the virus with the cells. After washing with PBS twice, the cells were resuspended with a 1640 complete medium containing 0.25 μg/mL TPCK pancreatin, and then incubated in a 39° C. incubator for 6 h. The PBMCs of a cell quantity being 2×10$^6$ infected with the recombinant H5N8-mApple virus were respectively incubated lucifugally with an FITC labeled mouse anti-KUL01 monoclonal antibody (purchased from SouthernBiotech) and an FITC labeled mouse anti-NP monoclonal antibody (purchased from Abcam) (containing 0.02% saponin) at 4° C. for 30 min.

After washing with PBS twice, the stained cells were analyzed with a flow cytometer (purchased from Beckman Coulter), identified as an infection group. The PBMC treated with PBS and stained in the same way was identified as a control group.

Figure 9:
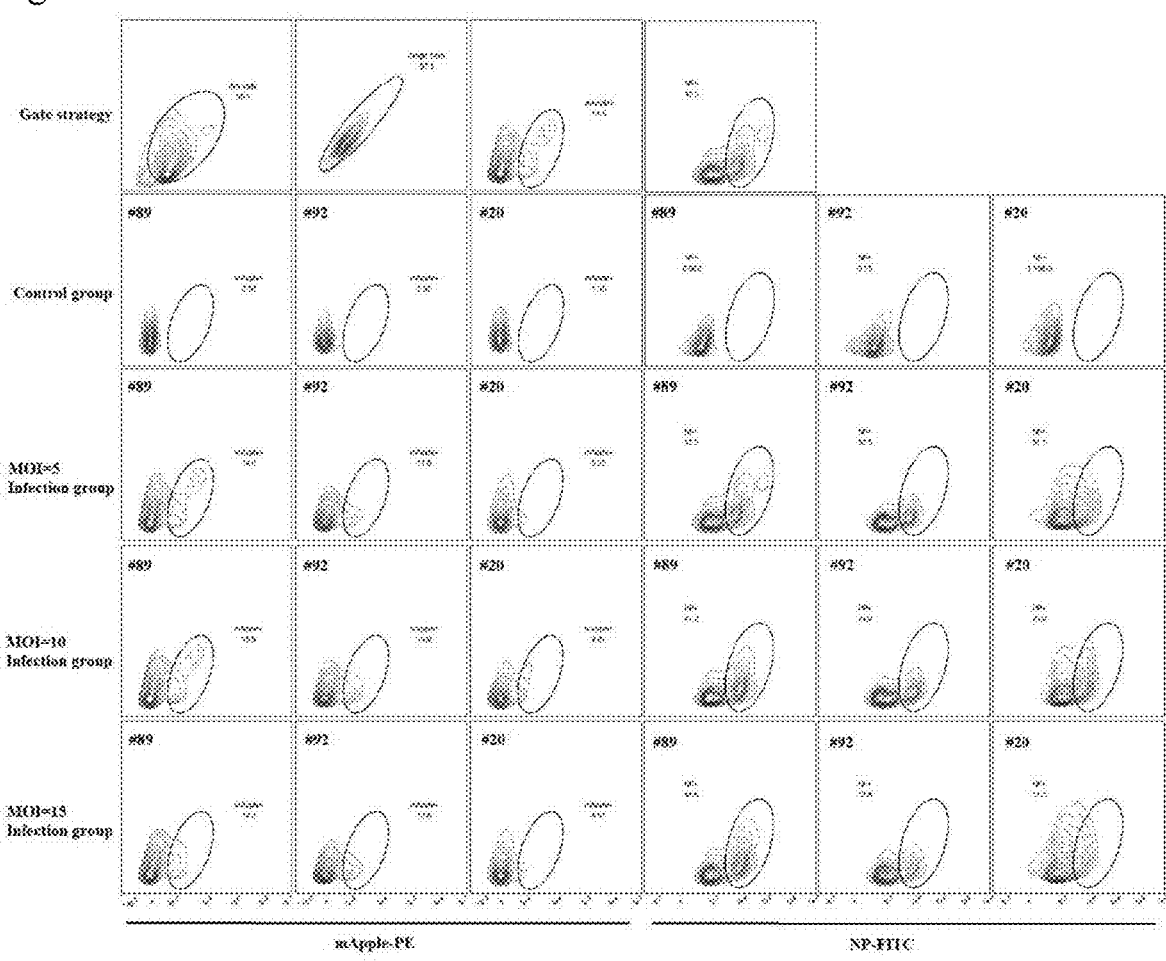
FIG. 9 is a contour plot for mApple positive and NP positive cell populations which are detected after peripheral blood mononuclear cells (PBMCs) of a recombinant H5N8-mApple virus infection group infected in vitro at different MOIs and a control group in an embodiment of the present disclosure.
Figure 10:
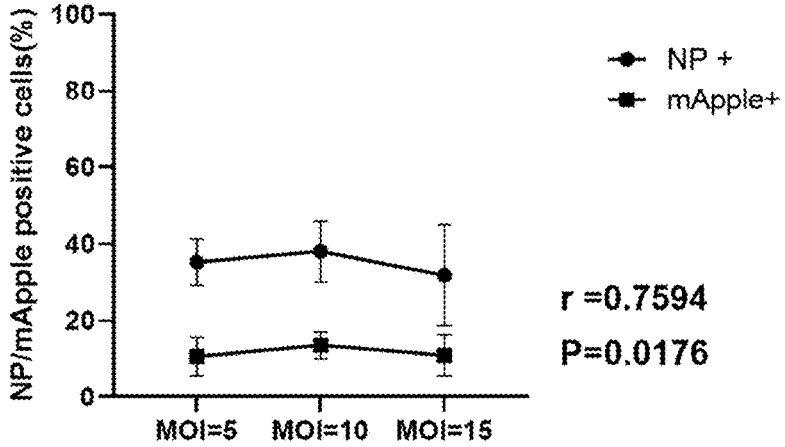
FIG. 10 is a diagram showing a proportion detection result for mApple positive and NP positive cell populations after peripheral blood mononuclear cells (PBMCs) are infected with a recombinant H5N8-mApple virus in vitro at different MOIs in an embodiment of the present disclosure.
Figure 11:
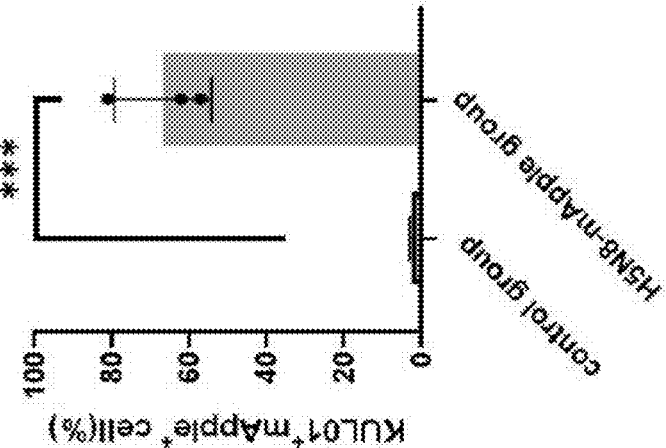
FIG. 11 is a proportion diagram for infected monocytes/macrophages ($mApple^+KUL01^+$) after peripheral blood mononuclear cells (PBMCs) are infected with a recombinant H5N8-mApple virus in vitro at MOI of 10 in an embodiment of the present disclosure, wherein the upper diagram is a contour plot for mApple and KUL01 double positive cells; and the lower diagram is a proportion detection result diagram for the mApple and KUL01 double positive cells.
Figure 11:
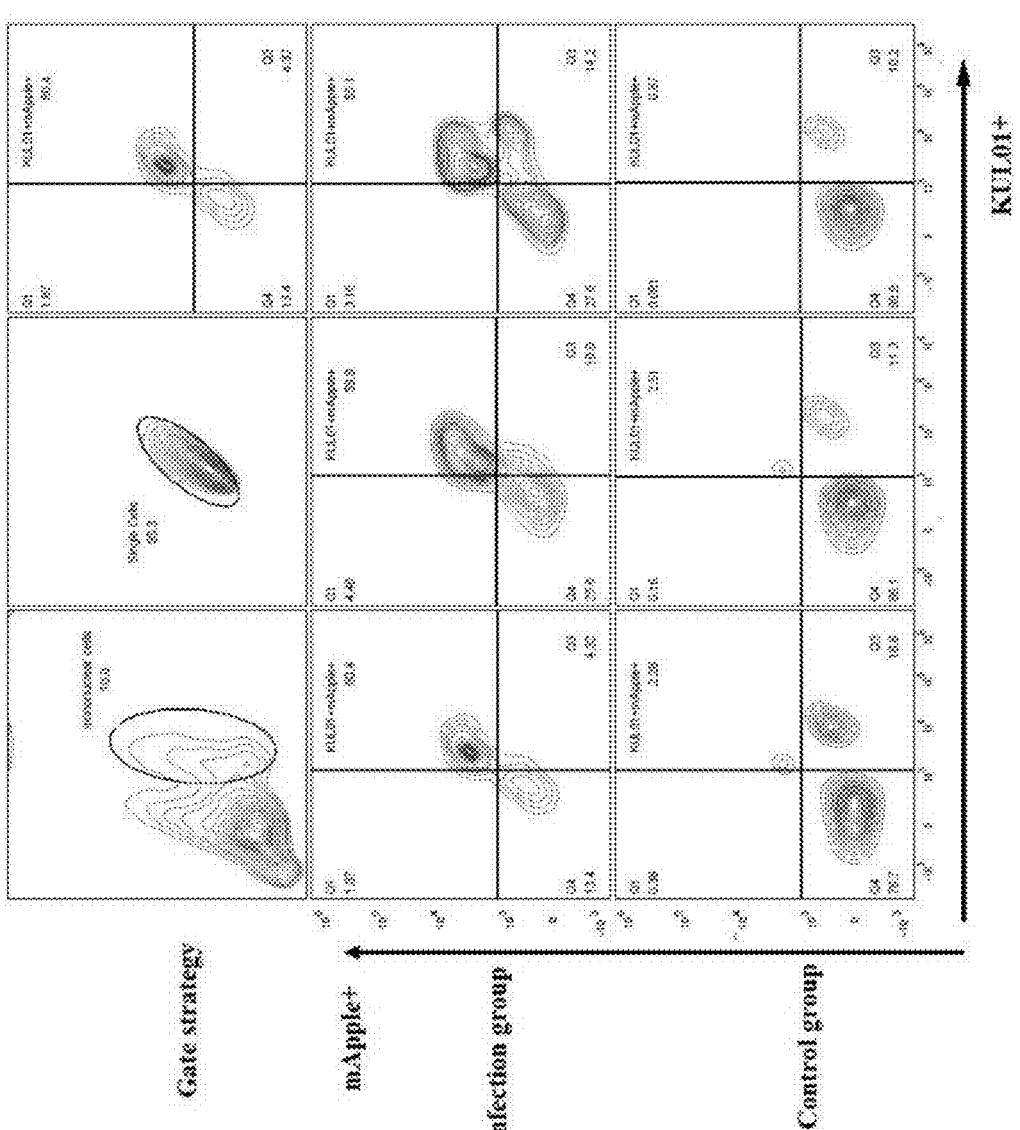

The detection results are shown in FIGS. 9, 10 and 11.

For the PBMCs of the SPF chicken infected in vitro with the recombinant H5N8-mApple virus, a correlation coefficient for an NP positive rate and an mApple positive rate is r>0.5 (r=0.7594); and P value is less than 0.05 (P=0.0176) through statistical analysis, indicating there is significant correlation between the two rates. Therefore, mApple is useful as an index for detecting the infection of the recombinant virus. At MOI of 10, the recombinant virus had the optimal infection efficiency, and the proportion of the mApple positive cells was 11.8%-13.6% (see FIGS. 9 and 10). In addition, in the experiment for infecting the PBMCs in vitro with the recombinant H5N8-mApple virus, the proportion of infected monocytes/macrophages (KUL01$^+$ mApple$^+$) was high as 55.1%-80.4% (see FIG. 11), which indicated that the monocytes/macrophages of the chicken are also important target cells for injection of the avian influenza virus.

The embodiments of the present disclosure have been described in detail with reference to the drawings above, but the present disclosure is not intended to be limited by the abovementioned embodiments, and various changes may be made within the knowledge scope possessed by those skilled in the art without departing from the purpose of the present disclosure. In addition, the embodiments of the present disclosure and the features in the embodiments may be combined with each other without conflict.

The invention claimed is:

1. A recombinant influenza nonstructural (NS) protein, comprising the amino acid sequence from positions 1 to 217 of SEQ ID NO: 2, the amino acid sequence of an mApple fluorescence reporter gene, and the amino acid sequence from positions 480 to 600 of SEQ ID NO: 2, linked in order.

2. A recombinant H5N8 subtype avian influenza virus carrying an mApple fluorescence reporter gene, having a genomic RNA composed of eight independent genomic RNA sequences shown in 1) and 2):

1) the following 7 genomic RNA sequences of a wild H5N8 subtype avian influenza virus: a genomic RNA encoding a HA protein, a genomic RNA encoding an NA protein, a genomic RNA encoding an M protein, a genomic RNA encoding a PA protein, a genomic RNA encoding a PB1 protein, a genomic RNA encoding a PB2 protein, and a genomic RNA encoding an NP protein; and 2) a genomic RNA encoding an NS protein, comprising the amino acid sequence from positions 1 to 217 of SEQ ID NO: 2, the amino acid sequence of an mApple fluorescence reporter gene, and the amino acid sequences from positions 480 to 600 of SEQ ID NO: 2, linked in order.

3. The recombinant H5N8 subtype avian influenza virus according to claim 2, wherein the wild H5N8 subtype avian influenza virus is H5N8 subtype avian influenza viral strain A/chicken/Guangdong/JM01/2020.

4. The recombinant H5N8 subtype avian influenza virus according to claim 2, wherein the amino acid sequence of the mApple fluorescence reporter gene is as shown from positions 222 to 457 of SEQ ID NO: 2.

5. The recombinant H5N8 subtype avian influenza virus according to claim 2, wherein the nucleotide sequence encoding the mApple fluorescence reporter gene is as shown from positions 711 to 1418 of SEQ ID NO: 1.

6. A biological material, comprising any one selected from the group consisting of:

A1: a nucleic acid molecule encoding the NS protein according to claim 1;

A2: an expression cassette containing the nucleic acid molecule of A1, a promoter and a transcription termination sequence;

A3: a recombinant vector obtained by inserting the nucleic acid molecule of A1 into an expression vector;

A4: a recombinant microorganism transfected with the nucleic acid molecule of A1;

A5: a transgenic cell line transfected with the nucleic acid molecule of A1; and A6: a recombinant virus carrying the nucleic acid molecule of A1.

7. The biological material according to claim 6, wherein the nucleic acid molecule of A1 comprises a nucleic acid molecule comprising the nucleotide sequence from positions 1 to 710 of SEQ ID NO: 1, the nucleotide sequence encoding the mApple fluorescence reporter gene, and the nucleotide sequence from positions 1419 to 1876 of SEQ ID NO: 1, linked in order.

8. A method for constructing the recombinant H5N8 subtype avian influenza virus according to claim 2, comprising:

transfecting an isolated cell with a recombinant expression vector combination capable of expressing cDNA fragments corresponding to the eight genomic RNA sequences as defined in claim 2; culturing the isolated cell and inoculating a chicken embryo with liquid from the cultured isolated cell; and culturing the chicken embryo to obtain the recombinant H5N8 subtype avian influenza virus carrying the mApple fluorescence reporter gene.

9. The method according to claim 8, wherein the isolated cell comprises an isolated mammalian cell.

10. The method according to claim 9, wherein the isolated mammalian cell is a 293T cell, a COS7 cell, an MDCK cell, a VERO cell, a WI-38 cell, an HL-8 cell, or a Hela cell.

* * * * *

SEQUENCE LISTING

```
Sequence total quantity: 2
SEQ ID NO: 1             moltype = DNA  length = 1897
FEATURE                  Location/Qualifiers
source                   1..1897
                         mol_type = other DNA
                         organism = synthetic construct
SEQUENCE: 1
cgacctccga agttggggg gagcaaaagc agggtgacaa aaacataatg gataccaaca      60
ctatgctaag ctttcaggta gactgttttc tttggtatgt ccgcaaacga ttcgcagacc     120
aagaactggg tgatgcccct ttccttgacc ggcttcgccg agatcagaag tctttaagag     180
gaagaggcac cactcttggt ctgagcatcg aagcagctac tcgtgaggga aagcagatag     240
tgaagcgaat tctgaaggaa gagtctgatg aggcacttaa aatgactgtt gcttcaggtc     300
cgtcttcacg ctacctaact gatatgactc ttgaagagat gtcaagggac tggttcatgc     360
tcatgcccaa acggaaagtg gcaggtccac tttgcatcaa aatggaccag gcaataatgg     420
ataaaaacat catattgaaa gcaaacttca gtgtaatttt caaccggctg gaagctctaa     480
tactacttcg agctttcaca gaagaaggag caattgtggg agaaatctca ccgttacctt     540
cttttccagg acatactgat gaggatgtca aaaatgcaat tgggggtcctc atcggagggc     600
ttgaatggaa taataacaca gttcgggtct ctgaaactct acagagattc gcttggagaa     660
acagtgatga ggatgggaga ccttcactcc ctccaaaggg atccggtgga atggtgagca     720
agggcgagga gaataacatg gccatcatca aggagttcat gcgcttcaag gtgcacatgg     780
agggctccgt gaacggccac gagttcgaga tcgagggcga gggcgagggc cgcccctacg     840
aggcctttca gaccgctaag ctgaaggtga ccaagggtgg cccctgccc ttcgcctggg     900
acatcctgtc ccctcagttc atgtacggct ccaaggtcta cattaagcac ccagccgaca     960
tccccgacta cttcaagctg tccttccccg agggcttcag gtgggagcgc gtgatgaact    1020
tcgaggacgg cggcattatt cacgttaacc aggactcctc cctgcaggac ggcgtgttca    1080
tctacaaggt gaagctgcgc ggcaccaact tcccctccga cggcccctgta atgcagaaga    1140
agaccatggg ctgggaggcc tccgaggagc ggatgtaccc cgaggacggc gccctgaaga    1200
gcgagatcaa gaagaggctg aagctgaagg acggcggcca ctacgccgcc gaggtcaaga    1260
ccacctacaa ggccaagaag cccgtgcagc tgcccggcgc ctacatcgtc gacatccagt    1320
tggacatcgt gtcccacaac gaggactaca ccatcgtgga acagtacgaa cgcgccgagg    1380
gccgccactc caccggcggc atggacgagc tgtacaaggg atccggcgcc accaacttca    1440
gcctgctgaa gcaggccggc gacgtggagg agaacccagg ccccatggat accaacacta    1500
tgctaagttt ccaggacata ctgatgagga tgtcaaaaat gcaattgggg tcctcatcgg    1560
agggcttgaa tggaataata acacagttcg gtctctgaa actctacaga gattcgcttg    1620
gagaaacagt gatgaggatg ggagaccttc actccctcca aagtagaaac ggaaaatggc    1680
gagaacaatt gggtcagaag tttgaagaaa taagatggct gattgaagaa gtgcgacata    1740
gactgaagat tacagaaaat agcttcgaac agataacgtt tatgcaagcc ttacaactat    1800
```

-continued

```
tgcttgaagt ggaacaagag ataagaactt tctcgtttca gcttatttga tgataaaaaa  1860
caccctttgtt tctactaata acccggcggc ccaaaat                           1897

SEQ ID NO: 2          moltype = AA  length = 600
FEATURE               Location/Qualifiers
source                1..600
                      mol_type = protein
                      organism = synthetic construct
SEQUENCE: 2
MDTNTMLSFQ VDCFLWYVRK RFADQELGDA PFLDRLRRDQ KSLRGRGTTL GLSIEAATRE   60
GKQIVKRILK EESDEALKMT VASGPSSRYL TDMTLEEMSR DWFMLMPKRK VAGPLCIKMD   120
QAIMDKNIIL KANFSVIFNR LEALILLRAF TEEGAIVGEI SPLPSFPGHT DEDVKNAIGV   180
LIGGLEWNNN TVRVSETLQR FAWRNSDEDG RPSLPPKGSG GMVSKGEENN MAIIKEFMRF   240
KVHMEGSVNG HEFEIEGEGE GRPYEAFQTA KLKVTKGGPL PFAWDILSPQ FMYGSKVYIK   300
HPADIPDYFK LSFPEGFRWE RVMNFEDGGI IHVNQDSSLQ DGVFIYKVKL RGTNFPSDGP   360
VMQKKTMGWE ASEERMYPED GALKSEIKKR LKLKDGGHYA AEVKTTYKAK KPVQLPGAYI   420
VDIKLDIVSH NEDYTIVEQY ERAEGRHSTG GMDELYKGSG ATNFSLLKQA GDVEENPGPM   480
DTNTMLSFQD ILMRMSKMQL GSSSEGLNGI ITQFGSLKLY RDSLGETVMR MGDLHSLQSR   540
NGKWREQLGQ KFEEIRWLIE EVRHRLKITE NSFEQITFMQ ALQLLLEVEQ EIRTFSFQLI   600
```